United States Patent [19]

Bertolini et al.

[11] Patent Number: 5,196,440
[45] Date of Patent: Mar. 23, 1993

[54] COMPOUNDS ACTIVE AS INHIBITORS OF THE CHOLESTEROL BIOSYNTHESIS

[75] Inventors: Giorgio Bertolini, Sesto San Giovanni; Cesare Casagrande, Arese; Francesco Santangelo, Milan, all of Italy

[73] Assignee: Zambon Group S.p.A., Vicenza, Italy

[21] Appl. No.: 519,444

[22] Filed: May 4, 1990

Related U.S. Application Data

[63] Continuation-in-part of Ser. No. 385,369, Jul. 27, 1989, Pat. No. 4,940,800.

[30] Foreign Application Priority Data

Jul. 29, 1988 [IT] Italy .................. 21542 A/88

[51] Int. Cl.$^5$ .................. C07D 487/00; C07D 401/00; A61K 31/44; A61K 31/415
[52] U.S. Cl. ........... 514/339; 548/304.7, 306.1, 310.1; 546/271; 514/394; 556/437; 556/428
[58] Field of Search ........ 548/327; 546/271; 514/339, 394; 556/437, 428

[56] References Cited

U.S. PATENT DOCUMENTS

| 4,613,610 | 9/1986 | Wareing | 548/327 |
| 4,925,853 | 5/1990 | Smith et al. | 548/327 |

FOREIGN PATENT DOCUMENTS

| 0179559 | 4/1986 | European Pat. Off. | 548/327 |
| 0244364 | 11/1987 | European Pat. Off. | 548/327 |
| 8607054 | 12/1986 | PCT Int'l Appl. | 548/327 |

Primary Examiner—Mary C. Lee
Assistant Examiner—Robert C. Whittenbaugh
Attorney, Agent, or Firm—Stevens, Davis, Miller & Mosher

[57] ABSTRACT

The compounds of formula

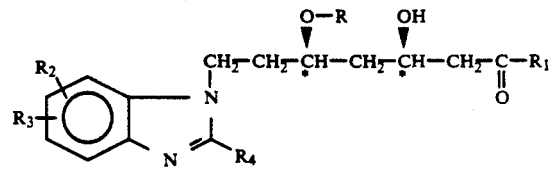

wherein R, $R_1$, $R_2$, $R_3$, and $R_4$ have the meanings given in the specification, as described.

The compounds of formula I are active as inhibitors of the enzyme HMG-CoA reductase and can be used in therapy as anti-hypercholesterolemics.

5 Claims, No Drawings

COMPOUNDS ACTIVE AS INHIBITORS OF THE CHOLESTEROL BIOSYNTHESIS

This application is a continuation-in-part application of our copending application Ser. No. 385,369, filed on Jul. 27, 1989 now U.S. Pat. No. 4,940,800.

The present invention concerns pharmaceutically active compounds and more particularly it concerns compounds endowed with anti-ateroschlerotic activity which inhibit hydroxymethyl-glutaryl-CoA reductase (HMG-CoA reductase), an enzyme which controls a key-step in the synthesis of cholesterol.

A compound known as Nevinolin (Merk Index, 10th Edition, No. 6042, page 883) was isolated from the metabolytes of fungi like *Monascus ruber* and *Aspergillus Terreus* and was recognized to be active in controlling and inhibiting enzyme HMG-CoA reductase which is responsible for the biosynthesis of cholesterol.

An object of the present invention is to provide a compound of formula:

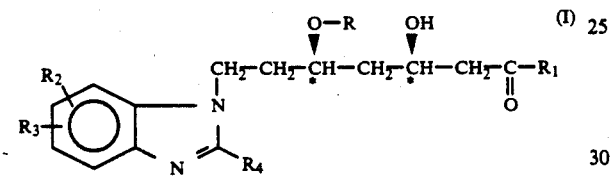

wherein
R represents a hydrogen atom;
$R_1$ represents a hydroxy or an $OR_5$ group where $R_5$ represents a $C_1$-$C_4$ alkyl or benzyl; or, R and $R_1$ together are a single bound between the oxygen and carbonyl;
$R_2$, $R_3$ and $R_4$, equal to or different from each other, represent hydrogen atoms, $C_1$-$C_5$ alkyl or alkoxy, halogen atoms, $CF_3$, aryl, heteroaryl, phenoxy, benxyloxy, amino, mono or dialkylamino having 1 to 4 carbon atoms in the alkyl moiety;
the carbon atoms marked by an asterisk have conempo-raneously r or S configuration and have therefor relative configuration syn; and when $R_1$ is hydroxy, the salts thereof with pharmaceutically acceptable bases.

The compound of formula I are capable of inhibiting the activity of the enzyme HMG-CoA reductase and therefore are useful as pharmaceuticals in the anti-hypercholesterolemic therapy, in the treatment of ateroschlerosis and hyperlipemia.

The compounds of formula I exist in two forms, an open form when R=H (I=A) and a closed form (I-B) easily interconvertible which proved to be both pharmaceutically useful

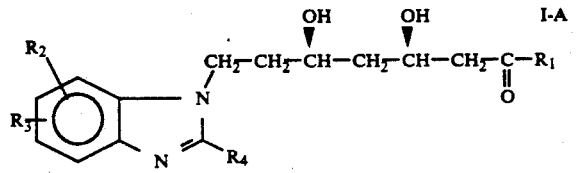

($R_1$ = OH, $OR_5$)

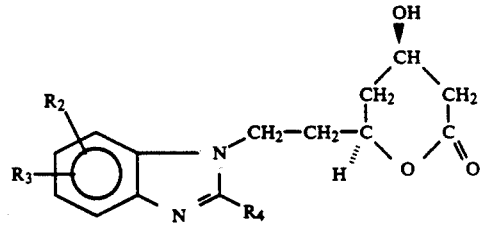

Having regard to R2, R3 and R4, preferred meanings of aryl and heteroaryl are phenyl optionally substituted by halogen and 5–6 membered heteroaryl rings wherein the hetero atom is nitrogen. Typical examples are phenyl, 2- and 4-bromo-, -chloro-and -fluoro-phenyl, pyrrolyl and pyridyl.

The preparation of the compounds of formula I is carried out by reacting a benzimidiazole of formula

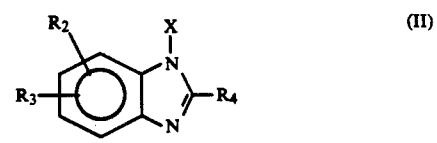

wherein $R_2$, $R_3$ and $R_4$ have the above reported meanings and X represents a hydrogen atom or an alkali metal (preferably lithium or sodium) or else a tetraalkylammonium group, with a compound of formula

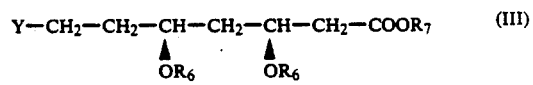

wherein
$R_6$ represent hydroxy protecting groups selected among trisubstituted silyl radicals;
$R_7$ represents $C_1$-$C_4$ alkyl or benzyl;
Y represents a leaving group or a group convertible into a leaving groups selected among chlorine, bromine or iodine atom, $C_1$-$C_4$ alkylsulphonate, optionally fluorinated arylsulphonate, hydroxy and triphenylmethyloxy.

The compounds of formula I are known or easily preparable benzimidazoles.

The compounds of formula III, on the contrary, are new compounds and are a further object of the present invention; their preparation is described hereinbelow.

The reaction between compound II and compound III is carried out in an inert solvent selected, in particular, among dipolar aprotic solvents optionally in admixture with a chlorinated solvent, at a temperature of from −20° C. to 50° C. and in anhydrous conditions.

From condensation of compound II with compound III, the compounds of formula I-A in which the hydroxy groups are protected as $OR_6$ and in the form of esters ($R_1$=$OR_5$) are obtained.

Deprotection of the hydroxy groups according to known procedures (e.g. fluorides in acetic acid) and, when desired, hydrolisis of the ester group afford the compounds I-A wherein $R_1$=$OR_5$ and $R_1$=OH, respectively.

These latters, when desired, may be salified according to known procedures, by treatment with a suitable base.

In turn, the compounds I-B are obtained by treating the product of the condensation of compound II with compound III, with aqueous hudrofluoric acid in the presence of organic solvents soluble in water (e.g. acetonitrile) at a temperature compresed between 0° C. and 70° C.

The salts of the compounds of formula I may also be obtained by treatry a compound of formula I-B with a base.

The preparation of the compounds of formula III is carried out according to the reactions reported in Scheme 1 and commented in the following Scheme 1.

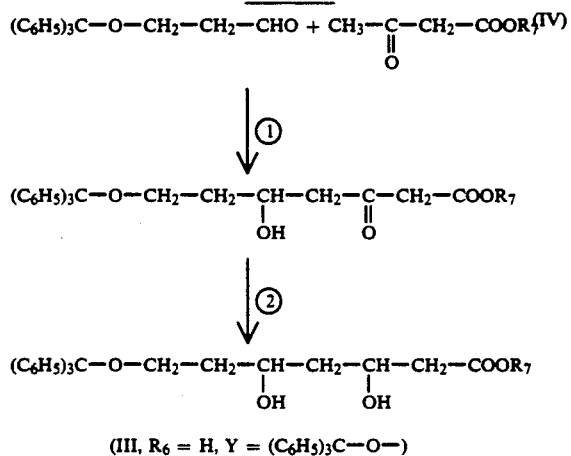

(III, $R_6$ = H, Y = $(C_6H_5)_3C-O-$)

Reaction 1 of Scheme 1 consists in reacting 3-hydroxypropionaldehyde protected or the hydroxy group as triphenylmethylether, with an acetoacetic ester. It will be apparent to the skilled in the art that instead of triphenylmethyl other hydroxy protecting groups can be used.

The reaction is carried out by preparing *in situ* the dianion of the acetoacetic ester by treatment of the latter with strong bases (lithium diisopropylamide, sodium hydride, lithium butyl) and by addition of a solution of the protected propionaldehyde in an ether solvent (tetrahydrofuran, dimethoxyethane) at a temperature of from −15° C. to 30° C. in anhydrous conditions and under an inert gas atmosphere.

Similar reactions have been described in the work published on Can. J. Chem., 52, 2157, (1974).

Thereby compound IV is obtained which is then stereoselectively reduced (reaction 2 of Scheme 1) affording compound III wherein $R_6$=H and Y=$(C_6H_5)_3C-O-$.

The stereospecific reduction is carried out by using a boron hydride (preferably of sodium or zink) optionally in the presence of trialkyl boranes (e.g. triethyl borane) or alkoxy-dialkylboranes (e.g. methoxy-diethylborane) in a solvent inert in the reaction conditions, e.g. an alcohol (methanol, ethanol) or an ether (dimethoxyethane) or their mixtures, under an inert atmosphere and at a temperature of from −80° C. to 30° C.

The remaining compounds of formula III are prepared from the compound III wherein $R_6$=H and Y=$(C_6H_5)_3C-O-$.

Thus, for example, the hydroxy groups may be protected by silylation using the corresponding silyl chloride, preferably a hindered silylating agent such as diphenyl-ter.butyl-silyl chloride, in the presence of a base and in an inert solvent.

The conversion of the group Y=$(C_6H_5)C-O-$ into other groups comprised in the meanings of Y is carried out by known methods.

For example by treatment with strong acids in a inert solvent the deprotection of the hydroxy group is obtained and therefore the compounds of formula III wherein Y=OH are obtained.

The reaction of these with sulphonic acid halides or anhydrides in an inert solvent and in the presence of a base affords the compounds of formula III wherein Y is an alkylsulphonyloxy or arylsulphonyloxy group.

The preparation of the compounds of formula III wherein Y is a chlorine, bromine or iodine atom can be carried out from the corresponding alcohol (III Y=OH) by known methods, for example by reaction with $Cl_2$, $Br_2$ or $I_2$ in the presence of a triphenyl phosphine in an inert solvent and at a temperature of from 0° and 60° C.

An alternative process for the preparation of the compound of formula III wherein Y=OH, Br and I, employs as starting product a compound of formula

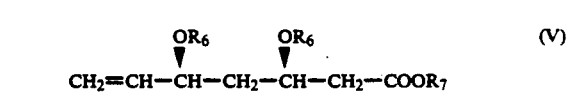

Hydroboration reaction of compound V with borane complexed with tetrahydrofuran, dimethylsulphide or amines, or with mono or dialkylboranes in an ether solvent at a temperature of from −20° C. to 60° C. affords a complex of compound V with borane, the decomposition of said complex by hydrogenperoxide and sodium hydroxide affords the compounds of formula III wherein Y=OH. Alternatively, the decomposition of the complex by bromine or iodine in an ether and alcohol solvent, followed by the addition of alkaline-earth alcoholates at a temperature of from 0° C. to 60° C. affords the compound of formula III wherein Y=Br or I.

The compounds of formula V are known, see for example U.S. Pat. No. 4,613,610.

As mentioned above, the compounds of formula I are inhibitors of the enzyme HMG-CoA reductase and therefore can be used in the pharmaceutical field as anti-hypercholesterolemic and anti-atheroschlerotic agents. The pharmacological activity of the compounds of the present invention was evaluated both in vitro and in vivo (see example 14).

For pratical use in the therapeutic field, the compounds of formula I are administered in the form of a suitable u pharmaceutical composition depending on the selected administration route.

Examples of solid pharmaceutical preparations for oral administration are capsules, tablets and granulates, of liquid pharmaceutical preparations for parenteral use are solutions and lyophilized forms to be diluted at the moment of their use.

The compositions contain one or more of the compounds of formula I as active ingredient together with suitable carriers and additives for pharmaceutical use in accordance with the type of composition.

The preparation of the composition is carried out by conventional procedures.

When desired, in the composition beside the compound of formula I another active ingredient may be added. Particularly useful are the biliary acid sequestrants, the nicotinic acid derivatives and the inhibitors of cholesterolacyltransferase (ACAT).

The dose of the compound of formula I to be administered varies depending on various factors such as the selected type of composition, the symptoms and the age of the patient.

The daily dose will generally be comprised from 10 and 500 mg to be administered as in one dose or more repeated doses.

With the aim of better illustrating the present invention the following example are given.

EXAMPLE 1

Preparation of ethyl 5-hydrossy-7-trityloxy-3-oxo heptanoate

Ethyl acetoacetate (18 ml; 143.7 mmols) was added to a suspension of rhodium hydride at 50% in mineral oil (4.1 g, 172.4 mmols) in tetrahydrofuran (210 ml) at 0° C. and under a nitrogen atmosphere, by keeping the temperature at about 0° C. After 10 minutes, a solution 1.6M of butyl lithium in hexane (94 ml, 150.8 mmols) was added slowly.

After 10 further minutes at 0° C. a solution of 3-trityloxypropionaldehyde (50 g, 158 mmols) in tetrahydrofuran (70 ml) was rapidly added. After stirring for 10 minutes at the same temperature it was diluted with 50 ml of Hcl 6N and with 300 ml of an ammonium chloride saturate solution. The product was estracted with diethyl ether (1 l+3×300 ml).

The combined organic phases were washed with a sodium chloride saturate solution (2×500 ml), dried or anhydrous sodium sulphate and evaporated under vacuum affording 67.6 g of an oily crude which was used directly in the subsequent reduction.

An analytical sample was prepared by column chromatography on silica gel (70–230 mesh); eluant, petroleum ether:ethyl acetate=8:2).

1HNMR (300 MHz, CDCl$_3$): delta (ppm): 1.25 (3H, t); 1.65–1.90 (2H; m); 2.64 (1H, dd); 2.68 (1H, dd); 3.23 (1H, m); 3.35 (1H, m); 3.46 (2H, s); 4.18 (2H, q); 4.27 (1H, m); 7.20–7.35 (9H, m); 7.40–7.45 (6H, m).

EXAMPLE 2

Preparation of ethyl (Syn)-3.5-dihidroxy-7-trityloxy-heptonoate

A solution of rhodium boron hydride (9.3 g, 246 mmols) in absolute ethanol (400 ml) pre-cooled at −70° C. was added to a solution of ethyl 5-hydroxy-7-titryloxy-3-oxo-heptonoate (55 g, 123 mmols) in absolute ethanol (1.2 ml) kept at −70° C. under nitrogen. The solution was stirred at that temperature from 1.5 hours then the solvent was evaporated and the residue was collected with methylene chloride (500 ml), a saturate solution of ammonium chloride (100 ml) and subsequently 1N hydrochloric acid up to pH 4–5 were slowly added to the mixture.

The mixture was extracted with methylene chloride (3×100 ml), the organic phase was dried on anhydrous sodium sulphate affording a crude (yellow oil) (52 g) which was purified by column chromatography on silica gel (70–230 mesh); eluant, petroleum ether/ethyl acetate by gradual variation of the ethylacetate percentage from 10% to 30%. A low melting product (21 g) was obtained.

$^1$H-NMR (300 MHz, CDCl$_3$): delta (ppm): 1.26 (3H, t); 1.50–1.90 (4H, m); 2.45–2.55 (2H, m); 3.22 (1H, m); 3.37 (1H, m); 3.72 (1H, d, exchange with D$_2$O); 3.94 (1H, d, exchange with D$_2$O); 4.06 (1H, m); 4.16 (2H, q); 4.27 (1H, m); 7.20–7.35 (9H, m); 7.40–7.45 (6H, m).

From the $^{13}$C-NMR analysis two series of signals were observed:

$^{13}$C-NMR syn steroisomer (75.4 MHz, CDCl$_3$): delta (ppm): 14.216 (q); 37.085 (t); 41.795 (t); 42.426 (t); 60.650 (t); 61.961 (t); 68.581 (d); 7.332 (d); 87.260 (s); 127.137 (d); 127.930 (d); 128.545 (d); 143.824 (s); 172.341 (s).

$^{13}$C-NMR anti stereoisomer (75.4 MHz, CDCl$_3$): delta (ppm): 14.216 (q); 36.680 (t); 41.584 (t); 42.673 (t); 65.522 (d); 68.694 (d); 87.409 (s); 127.930 (d); 128.545 (d); 143.739 (s); 172.714 (s).

By the composition of the signals belonging to the same carbon atom, a syn-anti ratio of 88:12 was determined.

EXAMPLE 3

Preparation of ethyl (Syn)-3,5-di-(diphenyl-ter.butyl-silyl-oxy)-7-trityloxy-heptanoate A solution of ethyl (syn)-3,5-dihydroxy-7-trityloxy-heptanoate (51 g; 113.8 mmol), ter.butyl-diphenyl-silyl chloride (70 ml, 273 mmols) and imidazole (31 g, 455 mmols) in dimethyl formamide (115 ml) was kept under stirring at 50° C. for 6 hours. The solution was poured in water (1 l) and extracted with diethyl ether (4×500 ml). The reunited ether phases were washed with water (500 ml), 0.1M hydrochloric acid (500 ml), a saturate sodium bicarbonate solution (500 ml) and a saturate sodium chloride solution (500 ml).

It was dried on anhydrous sodium sulphate and the solvent was evaporated thereby obtaining an oily product (113.8 g) which solidifies by treatment with diethyl ether.

After filtration, 62 g of a product (m.p. 141°–142° C.) were obtained.

From $^1$H-NMR (300 MHz) and $^{13}$C-NMR (75.4 MHz) it resulted to be the syn stereoisomer with a purity higher than 98%.

$^1$H-NMR (300 MHz, CDCl$_3$): delta 0.83 (9H, s); 0.92 (9H, s); 1.15 (3H, t); 1.40–1.75 (4H, m); 2.17 (1H, dd); 2.27 (1H, dd); 2.70–2.95 (2H, m); (2H, m); 3.87 (1H, m); 3.96 (2H, m); 4.35 (1H, m); 7.20–7.65 (35H, m).

$^{13}$C-NMR (75.4 MHz, CDCl$_3$) meaningful signals delta (ppm): 14.092 (q); 19.134 (s); 19.174 (s); 26.858 (q); 26.946 (q); 36.818 (t); 42.005 (t); 43.905 (t); 60.084 (t); 60.386 (t); 68.174 (d); 68.641 (d); 86.253 (s); 135.911 (d); 144.251 (s); 171.237 (s).

EXAMPLE 4

Preparation of ethyl (Syn)-3,5-di-(diphenyl-ter.butyl-silyloxo)-7-hydroxy-heptanoate p.toluene sulphonic acid (470 mg, 2.485 mmols) was added to a solution of ethyl 3,5-di-(diphenyl-ter.butyl-silyloxy)-7-trityloxy-heptanoate (23 g, 24.855 mmol) in ethanol/methylene chloride 1:1 (250 ml). The mixture was reflux heated for about 10 hours. Triethylamine (350 μl, 2.485 mmols) was added and the mixture was evaporated to dryness thereby obtaining a crude (colorless oil) which was purified by column chromatography on silica gel (70–230 mesh); eluant, petroleum ether-:ethyl acetate=9:1 thereby obtaining a product (13.7 g) (m.p. 75°–77° C.).

$^1$H-NMR (300 MHz, CDCl$_3$): delta (ppm): 0.93 (9H, s) (9H, s); 1.16 (3H, t); 1.35–1.60 (2H, m); 1.75–1.90 (2H, m); 2.17 (1H, dd); 2.23 (1H, dd); 3.35–3.55 (2H, m); 3.98 (2H, q); 4.06 (1H, m); 4.15 (1H, m); 7.30–7.45 (12H, m); 7.55–7.65 (8H, m).

EXAMPLE 5

Preparation of ethyl (Syn)-3,5-di-(diphenyl-ter.butyl-silyloxy)-7-iodo-heptanoate A solution of iodine (2 g, 8.05 mmols) in dimethyl formamide (5 ml) was slowly added so as to keep the temperature below 55° C., to a solution of ethyl (syn)-3,5-di-(diphenyl-silyloxy)-7-hydroxy-heptanoate (5 g, 7.32 mmols) and triphenyl phosphine (2.1 g, 8.05 mmols) in dimethyl formamide (10 ml) under nitrogen.

The mixture was stirred at room temperature for 1 hour. It was poured in 150 ml of water and 150 ml of diethyl ether. The phases were separated and the aqueous phase was extracted with diethyl ether (3×100 ml). The reunited ether phases were washed with a solution of sodium sulphite at 5%, with a saturate sodium bicarbonate solution and with water. The organic phase was dried on anhydrous sodium sulphate and the solvent was evaporated thereby obtaining a crude (7.7 g) which was purified by column chromatography on silica gel (70–230 mesh), eluant: petroleum ether/ethyl acetate 98:2, thus affording an oily product (4.78 g).

$^1$H-NMR (300 MHz, CDCl$_3$): delta (ppm): 0.95 (9H, s); 0.97 (9H, s); 1.18 (3H, t); 1.55–1.80 (4H, m); 2.27 (1H, dd); 2.30 (1H, dd); 2.78 (2H, m); 3.78 (1H, m); 4.00 (2H, m); 4.20 (1H, m); 7.30–7.45 (12H, m); 7.55–7.65 (8H, m).

EXAMPLE 6

Preparation of ethyl (Syn)-3,5-di-(diphenyl-ter.butyl-silyloxy)-7-(p.methyl-benzenesulphonyloxy)-heptanoate 4-methyl-benzenesulphonyl chloride (1.9 g, 9.87 mmols) was added at 0° C. to a solution of ethyl (syn)-3,5-di-(diphenyl-ter.butyl-silyloxy)-7-hydroxy-heptanoate (3.5 g, 5.12 mmols) in anhydrous pyridine (51 ml).

The mixture was left under stirring at room temperature for 15 hours. It was poured in water-ice (300 ml) and extracted with diethyl ether (4×100 ml). The reunited organic phases were washed with 1N HCl, with a saturate sodium bicarbonate solution and finally with a saturate sodium chloride solution.

After drying on anhydrous sodium sulphate, the solvent were evaporated thus affording a crude (oil) (4.2 g) which was purified by column chromatography on silica gel (70–230 mesh), eluant: petroleum ether/ethyl acetate by gradually increasing the percentage of petroleum ether from 5% to 20%.

The pure product as oil (3.2 g) was obtained.

$^1$H-NMR (300 MHz, CDCl$_3$): delta (ppm): 0.89 (9H, s); 0.90 (9H, s); 1.14 (3H, t); 1.40–1.60 (3H, m); 1.60–1.70 (1H, m); 2.17 (2H, d); 2.43 (3H, s); 3.70–3.90 (3H, m); 3.90–4.00 (2H, m); 4.12 (1H, m); 7.25–7.70 (24H, m).

EXAMPLE 7

Preparation of ethyl (Syn)-3,5-di-(diphenyl-ter.butyl-silyloxy)-7-trifluoromethylsulphonyloxy-heptanoate A solution of ethyl (syn)-3,5-di-(diphenyl-ter.butyl-silyloxy)-7-hydroxy-heptonoate (520 mg, 0.76 mmols) in carbon tetrachloride (1.8 ml) was added in about 45 minutes, at 0° C. under nitrogen, to a solution of trifluoromethanesulphonic anhydride (125 μl, 0.76 mmols) in carbon tetrachloride (2 ml). The mixture was stirred at 0° C. for 2 hours, the formed salts were filtered thereby obtaining a 2M solution of the product in carbon tetrachloride which was directly used for the subsequent alkylation reactions.

$^1$H-NMR (300 MHz, CDCl$_3$–CCl$_4$): delta (ppm): 0.91 (9H, s); 0.98 (9H, s); 1.16 (3H, t); 1.50–1.95 (4H, m); 2.29 (2H, d); 3.99 (2H, q); 4.12 (2H, m); 4.20 (1H, m); 4.32 (1H, m); 7.25–7.45 (12H, m); 7.50–7.75 (8H, m).

EXAMPLE 8

Preparation of ethyl (Syn)-3,5-di-(diphenyl-ter.butyl-silyloxy)-7-(1'-benzimidazolyl)-heptanoate Benzimidazole (72 mg, 0.60 mmols) was added at 0° C. under nitrogen to a suspension of NaH (24 mg, 0.60 mmols) in anhydrous dimethyl formamide (4 ml). The mixture was stirred at 50° C. for 30 minutes, it was brought to room temperature and a solution of ethyl (syn)-3,5-di-(diphenyl-ter.butyl-silyloxy)-7-(p.methyl-benzenesulphonyloxy)-heptanoate (500 mg, 0.60 mmols) in dimethyl formaldeide (2 ml) was added to it. The mixture was stirred overnight at room temperature. The reaction mixture was poured in water (30 ml) and extracted with diethyl ether (4×25 ml).

The reunited organic phases were washed with water, dried on anhydrous sodium sulphate and evaporated. The crude so obtained was purified by column chromatography on silica gel (70–250 mesh), eluant: petroleum ether:ethyl acetate=7:3, thereby obtained the pure product (260 mg) as oil. 7

$^1$H-NMR (300 MHz, CDCl$_3$): delta (ppm); 0.93 (9H, s); 1.04 (9H, s); 1.18 (3H, t); 1.56 (2H, m); 1.90 (2H, m); 2.36 (1H, dd); 2.41 (1H, dd); 3.75–4.00 (2H, m); 4.02 (2H, q); 4.05 (1H, m); 4.18 (1H, m); 7.00 (1H, d); 7.15–7.45 (15H, m); 7.55–7.65 (8H, m); 7.76 (1H, d).

The same product was also obtained by reacting benzimidazole with ethyl (syn)-3,5-di-(diphenyl-ter.butyl-silyloxy)-7-(trifluoromethylsulphonyloxy)-heptanoate or with ethyl (syn) -3,5-di-(diphenyl-ter.butyl-silyloxy)-7-iodo-heptanoate.

By operating in an analogous manner the following compounds were prepared:

Ethyl (Syn)-3,5-di-(diphenyl-ter.butyl-silyloxy)-7-(2-phenyl-1-benzimidazolyl)-heptanoate $^1$H-NMR (300 MHz, CDCl$_3$): delta (ppm): 0.90 (9H, s); 0.97 (9H, s); 1.15 (3H, t); 1.51 (2H, m); 1.78 (2H, m); 2.27 (2H, d); 3.98 (2H, q); 4.03 (3H, m); 4.18 (1H, m); 6.97 (1H, d); 7.15–7.45 (17H, m); 7.50–7.60 (10H, m); 7.79 (1H, d).

Ethyl (Syn)-3,5-di-(diphenyl-ter.butyl-silyloxy)-7-(2-methyl-1-benzimidazolyl)-heptanoate $^1$H-NMR (300 MHz, CDCl$_3$): delta (ppm): 0.90 (9H, s); 1.08 (9H, s); 1.17 (3H, t); 1.30–1.65 (2H, m); 1.90 (2H, m); 2.17 (3H, s); 2.39 (2H, m); 3.91 (2H, m); 4.01 (2H, q); 4.17 (2H, m); 6.88 (1H, d); 7.05–7.70 (23H, m).

Ethyl (Syn)-3,5-di-(diphenyl-ter.butyl-silyloxy)-7-(5.6-dimethyl-1-benzimidazolyl)-heptanoate $^1$H-NMR (300 MHz, CDCl$_3$): delta (ppm): 0.93 (9H, s); 1.04 (9H, s); 1.18 (3H, t); 1.57 (2H, m); 1.88 (2H, m); 2.31 (3H, s); 2.34 (2H, m); 2.36 (3H,s); 3.83 (2H, m); 4.01

(2H, q); 4.04 (1H, m); 4.18 (1H, m); 6.85 (1H, s); 7.20–7.65 (22H, m).

Ethyl (Syn)-3,5-di-(diphenyl-ter.butyl-silyloxy)-7-[2-(2-pyridyl)-1-benzimidazolyl]-heptanoate $^1$H-NMR (300 MHz, CDCl$_3$): delta (ppm): 0.91 (9H, s); 1.02 (9H, s); 1.13 (3H, t); 1.82 (2H, m); 1.90 (2H, m); 2.31 (2H, m); 3.98 (2H, m); 4.13 (1H, m); 4.37 (1H, m); 4.60 (2H, m); 6.97 (1H, d); 7.10–7.45 (16H, m); 7.55–7.65 (8H, m); 7.80 (2H, m); 8.33 (1H, m).

Ethyl (Syn)-3,5-di-(diphenyl-ter.butyl-silyloxy)-7-[2-(4-fluorophenyl)-1-benzimidazolyl]-heptanoate $^1$H-NMR (300 MHz, CDCl$_3$): delta (ppm): 0.89 (9H, s); 0.97 (9H? s); 1.15 (3H, t); 1.59 (2H, m); 1.73 (2H, m); 2.28 (2H, d); 3.98 (2H, q); 4.00–4.20 (4H, m); 6.95–7.00 (3H, m); 7.13–7.36 (12H, m); 7.43 (2H, m); 7.48–7.56 (10H, m); 7.77 (1H, d).

Ethyl (Syn)-3,5-di-(diphenyl-ter.butyl-silyloxy)-7-(2-isopropyl-1-benzimidazolyl)-heptanoate $^1$H-NMR (300 MHz, CDCl$_3$): delta (ppm): 0.86 (9H, s); 1.03 (9H, s); 1.12 (3H, t); 1.22 (3H, d); 1.25 (3H, d); 1.48 (2H, m); 1.88 (2H, m); 2.34 (2H, d); 2.81 (1H, m); 3.76–3.94 (2H, m); 3.97 (2H, q); 4.15 (2H, m); 6.83 (1H, d); 7.04 (1H, t); 7.10–7.45 (8H, m); 7.50 (4H, m); 7.60–7.70 (5H, m).

The same reaction, carried out on 5-fluoro-2-methyl-benzimidazole afforded two regioisomers which were separated by column chromatography.

Ethyl (Syn)-3,5-di-(diphenyl-ter.butyl-silyloxy)-7-(5-fluoro-2-methyl-1-benzimidazolyl)-heptanoate $^1$H-NMR (300 MHz, CDCl$_3$): delta (ppm); 0.89 (9H, s); 1.09 (9H, s); 1.18 (3H, t); 1.30–1.50 (2H, m); 1.90 (2H, m); 2.26 (3H, s); 2.43 (2H, m); 3.84–4.00 (2H, m); 4.02 (2H, q); 4.13 (1H, m); 4.20 (1H, m); 6.74 (1H, dd); 6.82 (1H, dt); 7.15–7.70 (21H, m).

Ethyl (Syn)-3,5-di-(diphenyl-ter.butyl-silyloxy)-7-(6-fluoro-2-methyl-1-benzimidazolyl)-heptanoate $^1$H-NMR (300 MHz, CDCl$_3$): delta (ppm): 0.90 (9H, s); 1.08 (9H, s); 1.18 (3H, t); 1.35–1.55 (2H, m); 1.91 (2H, m); 1.25 (3H, s); 3.87 (2H, m); 4.02 (2H, q); 4.13 (1H, m); 4.20 (1H, m); 6.63 (1H, dd); 6.92 (1H, dt); 7.15–7.70 (21H, m).

EXAMPLE 9

Preparation of trans-6-[2-(1-benzimidazolyl)-ethyl]-4-hydroxytetrahydropiran-2-one A solution of ethyl (syn)-3,5-di-(diphenyl-ter.butyl-silyloxy)-7-(1-benzimidozolyl)-heptanoate (200 mg) in a mixture of acetonitrile and hydrofluoric acid at 40% in water (5 ml) was stirred at 50° C. for 10 hours. Hydrofluoric acid was neutralized by solid sodium bicarbonate, the mixture was diluted with a small amount of water and with ethyl acetate (20 ml), the formed salts were filtered and the mixture was extracted with ethyl acetate (3×20 ml).

The combined organic phases were washed with a sature sodiun chloride solution, dried on anhydrous sodiun sulphate and evaporated. The obtained crude was collected with warm diethyl ether, it was cooled and filtered thereby obtaining the product (31 mg) (m.p.=188°–189° C.).

$^1$H-NMR (300 MHz, CDCl$_3$): delta (ppm): 1.55 (1H, m); 1.75 (1H, td); 2.02 (2H, m); 2.52 (2H, d); 4.10 (1H, m); 4.32 (2H, m); 4.51 (1H, m); 7.12 (1H, t); 7.17 (1H, m); 7.33 (1H, d); 7.62 (1H, d); 7.84 (1H, s).

Mass spectroscopy (chemical ionization, positive ions, isobutane): m/e 261 /M+1/+; 243.

By operating in an analogus manner, the following compounds were prepared:

Trans-6-[2-(2-phenyl-1-benzimidazolyl)-ethyl]-4-hydroxy-tetrahydropyran-2-one (m.p.=195°–196° C.)

$^1$H-NMR (300 MHz, DMSO-d$_6$): delta (ppm): 1.67 (1H, ddd); 1.76 (1H, td); 2.06 (2H, m); 2.36 (1H bd); 2.62 (1H, dd); 4.07 (1H, m); 4.43 (2H, m); 4.61 (1H, m); 5.18 (1H, d exchange with D$_2$O); 7.26 (1H, bt); 7.31 (1H, bt); 7.58 (3H, m); 7.67 (1H, bd); 7.70 (1H, bd); 7.79 (2H, m).

Mass spectrocopy (chemical ionization, positive ions, isobutane); m/e 337 [M+1]+; 319.

IR (Nujol) cm$^{-1}$; 1730, 1400, 1320, 745, 695.

Trans-6-[2-(2-methyl-1-benzimidazolyl-ethyl]-4-hydroxy-tetrahydropyran-2-one (m.p. 181°–183° C.)

$^1$H-NMR (300 MHz; DMSO-d$_6$): delta (ppm): 1.72 (1H, ddd); 1.80 (1H, bd); 2.05 (2H, m); 2.40 (1H, bd), 2.56 (3H, s); 2.67 (1H, dd); 4.11 (1H, m); 4.32 (2H, m); 4.55 (1H, m); 5.20 (1H, d, exchange with D$_2$O): 7.14 (1H, bt); 7.18 (1H, 7.50 (1H, bd); 7.53 (1H, db).

Mass spectroscopy (chemical ionization, positive ions, isobutane); m/e 275 [M+1]+; 257.

Trans-6-[2-(5,6-dimethyl-1-benzimidazolyl)-ethyl]-4-hydroxy-tetrahydropyran-2-one (m.p.=180°–181° C.)

$^1$H-NMR (300 MHz, CDCl$_3$): delta (ppm): 1.70 (1H, ddd); 1.91 (1H, td); 2.15 (2H, m); 2.35 (3H, s); 2.38 (3H, s); 2.68 (2H, d); 4.37 (3H, m); 4.65 (1H, m); 7.18 (1H, s); 7.49 (1H, s); 7.78 (1H, s).

Mass spectroscopy (chemical ionization, positive ions, isobutane): m/e 289 [M+1]+; 271.

Trans-6-[2-(2-pyridyl)-1-benzimidazolyl/ethyl]-4-hydroxy-tetrahydropyran-2-one (m.p.=168°–170° C.)

$^1$H-NMR (300 MHz, CDCl$_3$): delta (ppm): 1.79 (1H, ddd); 1.92 (1H, bd); 2.32 (2H, m); 2.61 (1H, dd); 2.74 (1H, dd); 4.37 (1H, m); 4.38 (1H, m); 5.00 (2H, m); 7.33 (4H, m); 7.55 (1H, d); 7.84 (2H, m); 8.41 (1H, d).

Mass spectroscopy (chemical ionization, positive, isobutane): m/e 338 [M+1]+; 320.

Trans-6-[2-[2-(4-fluorophenyl)-1-benzimidazolyl]-ethyl]-4-hydroxy-tetrahydropyran-2-one (m.p.=155°–6° C.).

$^1$H-NMR (300 MHz, CDCl$_3$): delta (ppm): 1.65 (1H, ddd); 1.81 (1H, td); 2.05 (2H, m); 2.56 (1H, dd); 2.45 (1H, dd); 4.30 (1H, m); 4.35–4.57 (2H, m); 4.63 (1H, m); 7.21 (2H, t); 7.32 (2H, m); 7.47 (1H, dd); 7.68 (2H, dd); 7.79 (1H, dd).

Mass spectroscopy (chemical ionization, positive ions, ammonia): m/e 355 [M+1]+; 337.

Trans-6-[2-(2-isopropyl-1-benzinidazolyl)-ethyl]-4-hydroxy-tetrahydropyran-2-one $^1$H-NMR (300 MHz, CDCl$_3$): delta (ppm): 1.42 (3H, d); 1.46 (3H, d); 1.76 (1H, ddd); 1.90 (1H, td); 2.12 (2H, t); 2.65 (1H, dd); 2.74 (1H, dd); 3.27 (1H, m); 4.30–4.50

(3H, m); 4.73 (1H, m); 7.20–7.28 (2H, m); 7.35 (1H, m); 7.73 (1H, m).

Mass spectroscopy (chemical ionization, positive ions, ammonia): m/e 303 [M+1]+; 285.

Trans-6-[2-(5-fluoro-2-methyl-1-benzimidazolyl)-ethyl]-4-hydroxy-tetrahydropyran-2-one (m.p.=154°–7° C.)

1H-NMR (300 MHz, DMSO): delta (ppm): 1.71 (1H, ddd); 1.80 (1H, td); 2.03 (2H, m); 2.40 (1H, dd); 2.56 (3H, s); 2.66 (1H, dd); 4.11 (1H, m); 4.32 (2H, m); 4.54 (1H, m); 5.20 (1H, d, exchange with $D_2O$); 7.05 (1H, dt); 7.33 (1H, dd); 7.52 (1H, dd).

Mass spectroscopy (chemical ionization, positive ions, ammonia): m/e 293 [M+1]+; 275.

Trans-6-[2-(6-fluoro-2-methyl-1-benzimidazolyl)-ethyl]-4-hydroxy-tetrahydropyran-2-one (m.p.=192°–4° C.)

1H-NMR (300 MHz, DMSO): delta (ppm); 1.72 (1H, ddd); 1.82 (1H, td); 2.03 (2H, m); 2.41 (1H, dd); 2.54 (3H, s); 2.66 (1H, dd); 4.11 (1H, m); 4.28 (2H, m); 4.54 (1H, m); 5.20 (1H, d, exchange with $D_2O$); 6.98 (1H, dt); 7.40 (1H, dd); 7.50 (1H, dd).

Mass spectroscopy (chemical ionization, positive, ammonia): m/e 293 [M+1]+; 275.

EXAMPLE 10

Preparation of ethyl (syn)-3,5-di-(diphenyl-ter.butyl-silyloxy)-7-hydroxy-heptanoate

Method A

A 1M solution of borane in tetrahydrofuran (600 µl; 0.6 mmols) was added in about 30 minutes at 0° C. under an inert atmosphere to a solution of ethyl (syn)-3,5-di-(diphenyl-ter.butyl-silyloxy)-hept-6-enoate (1 g, 1.5 mmols) in anhydrous tetrahydrofuran (8 ml).

After the addition, the mixture was stirred at room temperature for 3 hours, the excess borane was decomposed with a few drops of water and a solution of hydrogen peroxide at 15% (450 µl, 2.0 mmols) was added in 20 minutes at room temperature keeping the pH between 7 and 8 by the addition of an aqueous 3 N sodium hydroxide solution.

After 1 hour at room temperature, the reaction mixture was poured in water (25 ml) and extracted with diethyl ether (4×200 ml), the reunited organic phases were dried on anhydrous sodium sulphate and the solvent was evaporated thereby obtaining 0.96 g of a crude (colourless oil) which was purified by column chromatography on silica gel (230–400 mesh); eluant, petroleum ether:ethyl acetate=9:1, affording 0.27 g of the product (m.p. 75°–77° C.).

Method B

A 0.5M solution of 9-borabicyclononane in tetrahydrofuran (3.6 ml, 1.8 mmols) was added in 30 minutes at 0° C. under an inert atmosphere to a solution of ethyl (syn)-3,5-di-(diphenyl-ter.butyl-silyloxy)-hept-6-enoate (0.75 mmols) in anhydrous tetrahydrofuran (4 ml).

After the addition, it was stirred at 0°–5° C. for 16 hours, the excess of 9-borabicyclononane was decomposed with a few drops of water and a solution at 35% of hydrogen peroxide (0.89 ml, 9.15 mmols) was added in 20 minutes at 0° C., keeping the pH between 7 and 8 by adding a 3N aqueous solution of potassium hydroxide (0.37 ml).

After 3 hours at room temperature, the reaction mixture was poured into a sodium chloride saturate solution (30 ml) and extracted with ethyl acetate (4×15 ml). The reunited organic phases were washed with a 1M sodium thiosulphate solution, dried on anhydrous sodium sulphate and the solvent evaporated thereby obtaining a crude (0.76 g) (colourless oil) which was purified by column chromatography on silica gel (230–400 mesh); eluant, toluene/ethyl acetate=95:5 affording the product (0.38 g) (m.p. 75°–77° C.).

The physico-chemical characteristics of the product are the same as those reported in example 4.

EXAMPLE 11

Preparation of ethyl (syn)-3,5-di-(diphenyl-ter.butyl-silyl-oxy)-7-iodo-heptanoate

Method A

A 1M solution of borane in tetrahydrofuran (1.2 ml, 1.2 mmols) was added at 0° C. in 30 minutes to a solution of ethyl (syn)-3,5-di-(diphenyl-ter.butyl-silyloxy)-hept-6-enoate (2 g, 3.0 mmols) in anhydrous tetrahydrofuran (16 ml).

After the addition, the mixture was stirred at room temperature for 3 hours, the excess borane was then decomposed with anhydrous methanol (100 µl) and a 1M solution of iodine chloride in methanol (2 ml, 2 mmols) was added to it.

The mixture was stirred overnight at room temperature, poured into water (20 ml) and extracted with diethyl ether (4×20 ml).

The reunited organic phases were washed with 1M sodium thiosulphate solution, dried on anhydrous sodium sulphate and evaporated thereby obtaining a crude (2.06 g) (colourless oil) which was purified by column chromatography on silica gel (230–400 mesh); eluant, toluene/petroleum ether=1:1, affording the pure product (0.32 g) as oil.

Method B

A 0.5M solution of 9-borabicyclononane in tetrahydrofuran (3.6 ml, 1.8 mmols) was added at 0° C. in about 30 minutes to a solution of ethyl (syn)-3,5-di-(diphenyl-ter.butyl-silyloxy)-hept-6-enoate (0.5 g, 0.75 mmols) in anhydrous tetrahydroufuran (5 ml).

After the addition, the mixture was stirred at 0° C. for 16 hours, the excess of 9-borabicyclononane was decomposed with absolute ethanol (60 µl) and bis-sublimated iodine (0.65 g, 2.55 mmols) was added and thereafter a 0.87M solution of sodium ethoxide in ethanol (2.93 ml, 2.55 mmols) was added dropwise in about 30 minutes at 0° C.

The mixture was stirred overnight at room temperature, it was poured into a 1M sodium thiosulphate solution (30 ml) and extracted with diethyl ether (4×20 ml).

The reunited organic phases were dried on anhydrous sodium sulphate and evaporated thereby obtaining a crude (0.92 g) (dark oil) which was purified by column chromatography on silica gel (230–400 mesh) eluant toluene/petroleum ether 1:1, affording a chromatographically pure product (0.25) as oil.

The physico-chemical characteristics of the product are the same as those reported in Example 5.

EXAMPLE 12

Preparation of sodium (syn)-3,5-dihydroxy-7-(2-phenyl-1-benzimidazolyl)-heptanoate A 0.1N solution of sodium hydroxide (890 μl), 0.089 mmols) was added at room temperature to a solution of trans-6-[2-(2-phenyl-1-benzimidazolyl)-ethyl]-4-hydroxy-tetrahydropyran-2-one (30 mg, 0.089 mmols) in methanol (4.5 ml).

The mixture was stirred at this temperature for 3 hours, the solvent was evaporated, the residue was dissolved in water and extracted with diethylether ($2\times3$ ml), the aqueous solution was cooled at $-78°$ C. and lyophilized thereby obtaining the product (24 mg) (hygroscopic solid) pure by thin layer chromatography (eluant, methylene chloride/methanol/acetic acid =79:15:1).

$^1$H-MNR (300 MHz, D$_2$O): delta (ppm): 1.40–1.60 (2H, m); 1.77 (1H, m); 1.93 (1H, m); 2.18 (1H, dd); 2.24 (1H, dd); 3.61 (1H, m); 3.91 (1H, m); 4.37 (2H, m); 7.39 (2H, m); 7.60–7.75 (7H, m).

IR (KBr) cm$^{-1}$: 3400; 1575; 1400; 750; 700.

EXAMPLE 13

Preparation of ethyl trans-3,5-dihydroxy-7-(2-phenyl-1-benzimidazolyl)-heptanoate A mixture of ethyl (syn)-3,5-di-(diphenyl-ter.butyl-silyloxy)-7-(2-phenyl-1-benzimidezolyl)-heptanoate (120 mg, 0.139 mmols), glacial acetic acid (67 μ; 1.117 mmols) and tetrabutylammonium fluoride (1M solution in tetrahydrofuran, 1.117 mmols) was reflux heated for 7 hours.

The reaction mixture was poured into a sodium bicarbonate saturate solution (15 ml) and extracted with methylen chloride ($3\times15$ ml).

The reunited organic phases were washed with water (20 ml) dried an anhydrous sodium sulphate and evaporated thereby obtaining a crude (146 mg) which was purified by column chromatography on silica gel (230–400 mesh) eluant methylene chloride/ethyl acetate 7:3 affording the product (24 mg) as oil pure by thin layer chromatography (eluant, methylene chloride-/ethyl acetate=7:3).

$^1$H-MNR (300 MHz, CDCl$_3$): delta (ppm); 1.25 (3H, t); 1.38 (1H, bd); 1.55 (1H, m); 1.88 (2H, m); 2.38 (2H, m); 3.81 (1H, m); 4.14 (2H, q); 4.16 (1H, m); 4.36 (2H, m); 7.29 (2H, m); 7.48 (4H, m); 7.70 (2H, m); 7.80 (1H, m).

Mass spectropy (chemical ionization, positive ions, isobutane) m/e 383[M+1]$^+$.

EXAMPLE 14

Evaluation of the pharmacological Activity

Sprague Dowly male rats (100–125 g) were kept for 7 days in a light-dark controlled chamber and fed with a standard diet and water ad libitum.

The animals were sacrificed by beheading and livers were immediately used for the preparation of microsomes according to the method described by Shapiro and Rodwell (J. Biol.Chem.246, 3210 (1971)).

The microsome pellets were suspended in a phosphate buffer and stored at $-80°$ C.

In vitro HMG-CoA reductase activity

The activity of the enzyme was evaluated according to the method described by Goldstein and Brawn (Proc. Natu. Acad. Sci. USA 73, 2564 (1976)).

The incubation mixture (200 μ) was composed by: phosphate buffer 100 mM (pH 7.4), dithiotreitole 10 mM, EDTA 10 mM, NADP 25 mM, glucosium-6-phosphate 20 mM, glucosium-6-phosphate dehydrogenase 3 U/ml, ($^{14}$C)-HMG-CoA (New England Nuclear) 110 mM (0.08 uCi) and 600 ug of microsomial portions.

($^3$H)-mevalonalacton was used as interval standard.

The unreacted ($^{14}$C)-HMG-CoA was separated as described by Alberto et al. (Proc. Natu. Acad. Sci. ISA, 77, 3957 (1980)), by means of columns containing AG1-X8 formiate (Bio-rad) resins.

The ($^{14}$C)-mevalonolacton was then eluted by distilled water ($3\times750$ ul) directly in vials containing Picofluor-40 (Packard) (10 ml).

The radioactivity in the samples was measured by a Packard 4000 beta-counter.

Anti-hyperlipidemic activity in vivo

The activity was tested in comparison with nevinolin in non-lipidemic rabbits (Watanabe et al. ATH, 38, 27 (1971)).

The compounds were orally administered at the dose of 5 or 50 mg/kg/die and the treatment lasted 14 days.

At the end of the treatment blood samples were withdrawn for the plasma lipids dosage.

We claim:

1. A compound of the formula $$\underset{R_3}{\overset{R_2}{\diagdown}}\!\!\!\bigcirc\!\!\!\underset{N}{\overset{N}{\diagup}}\!\!\!\underset{R_4}{\overset{}{\diagdown}}\quad CH_2\text{--}CH_2\text{--}\overset{O-R}{\overset{\downarrow}{CH}}\text{--}CH_2\text{--}\overset{OH}{\overset{\downarrow}{CH}}\text{--}CH_2\text{--}\underset{O}{\overset{}{C}}\text{--}R_1 \quad (I)$$

wherein

R represents a hydrogen atom;

R$_1$ represents a hydroxy or an OR$_5$ group where R$_5$ represents a C$_1$–C$_4$ alkyl or benzyl; or R and R$_1$ together are a single bond between the oxygen or carbonyl;

R$_2$ and R$_3$, equal to or different from each other, represent hydrogen atoms, C$_1$–C$_5$ alkyl or alkoxy, halogen atoms, CF$_3$, phenoxy, benzyloxy, amino, or mono or dialkylamino having 1 to 4 carbon atoms in the alkyl moiety; and R$_4$ is phenyl which is unsubstituted or substituted by halogen or a pyrrolyl or pyridyl the carbon atoms marked by an asterisk have contemporaneously R or S configuration; and, when R$_1$ is hydroxy, a salt thereof with a pharmaceutically acceptable base.

2. A compound according to claim 1 having formula

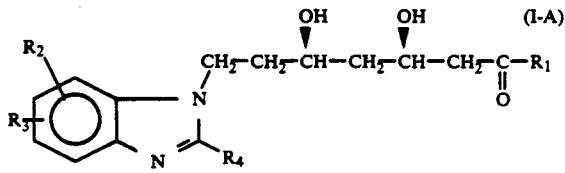

wherein $R_1$ is hydroxy or an $OR_5$ group; $R_2$, $R_3$, $R_4$ and $R_5$ have the meanings indicated in claim 1.

3. A compound according to claim 1 having formula

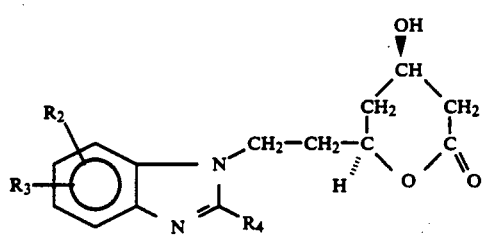

wherein $R_2$, $R_3$, and $R_4$ have the meanings indicated in claim 1.

4. A compound of the formula

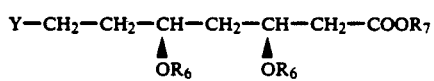

wherein
$R_6$ represents a diphenyl-ter.butyl-silyl;
$R_7$ represents $C_1$-$C_4$ alkyl or benzyl; and
Y represents OH or a leaving group selected from the group consisting of chlorine, bromine, iodine, a $C_1$-$C_4$ alkyl sulphonate, 4-methylbenzenesulfonyl, and triphenyl methoxy.

5. A pharmaceutical composition active as an inhibitor of the cholesterol synthesis comprising a cholesterol inhibiting amount of a compound of the formula

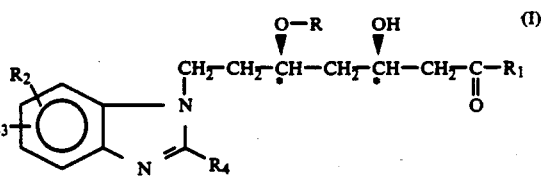

wherein
R represents a hydrogen atom;
$R_1$ represents a hydroxy or an $OR_5$ group wherein $R_5$ represents a $C_1$-$C_4$ alkyl or benzyl; or
  R and $R_1$ together are a single bond between the oxygen and carbonyl;
  $R_2$, $R_3$ and $R_4$, equal to or different from each other, represent hydrogen atoms, $C_1$-$C_5$ alkyl or alkoxy, halogen atoms, $CF_3$, phenyl, pyrrolyl or pyridyl, phenoxy, benzyloxy, amino, or mono or dialkylamino having 1 to 4 carbon atoms in the alkyl moiety;
the carbon atoms marked by an asterisk have contemporaneously R or S configuration; and, when $R_1$ is hydroxy, a salt thereof with a pharmaceutically acceptable base, together with a pharmaceutically acceptable excipient.

* * * * *